United States Patent [19]

Maeda

[11] Patent Number: 4,786,280
[45] Date of Patent: Nov. 22, 1988

[54] DESTRUCTION APPARATUS FOR SYRINGE

[76] Inventor: Taichi Maeda, 9-2, Kiyomizu 1 chome, Kokurakitaku, Kitakyushu-shi, Fukuoka, Japan

[21] Appl. No.: 48,693

[22] Filed: May 12, 1987

[51] Int. Cl.⁴ .................. A61M 5/00; B26F 3/00; B65H 35/00
[52] U.S. Cl. ..................... 604/110; 225/93; 225/97
[58] Field of Search .................. 604/110; 225/93, 97, 225/103

[56] References Cited

U.S. PATENT DOCUMENTS

| | | | |
|---|---|---|---|
| 3,736,824 | 6/1973 | Dunnican et al. | 225/93 X |
| 3,796,359 | 3/1974 | Dick | 225/93 |
| 4,332,323 | 6/1982 | Reenstierna | 604/110 X |

Primary Examiner—Allen M. Ostrager
Attorney, Agent, or Firm—Armstrong, Nikaido, Marmelstein & Kubovcik

[57] ABSTRACT

Provided is a syringe destruction apparatus comprising a syringe needle shearing section and a barrel breaking section, wherein the needle and barrel of a used syringe are broken by movable blades driven by a rotating cam plate to prevent the syringe from being reused, thereby it is possible to prevent a used syringe from being abused in narcotic crimes.

3 Claims, 3 Drawing Sheets

DESTRUCTION APPARATUS FOR SYRINGE

BACKGROUND OF THE INVENTION

The present invention relates to a syringe destruction apparatus having a simple structure.

A huge number of syringes are used in hospitals etc., and almost all of them are made of plastic materials and of the throw-away type.

Accordingly, the most syringes are discarded without reuse. However, if they are discarded while left intact, as they have been, there is a risk of them being reused by drug or narcotic addicts, resulting in increased narcotics-related crimes, and further, if virus, etc. adhered to syringes, there would be problems in that they could serve as mediums for infectious diseases.

Further, although it is possible to break up each syringe with pinchers, a hammer or the like as it is used, it is troublesome to destroy so many syringes, and therefore, it has been impractical to destroy a huge number of syringes. Further, on some occasions a large crusher has been used to smash a huge number of syringes into small pieces, but there has also been a problem in that a large crusher cannot be installed in a hospital which uses a small number of syringes.

SUMMARY OF THE INVENTION

One object of the present invention is to provide a syringe destruction apparatus which is relatively small and simple but which can break syringe needles and barrels so that it is impossible to reuse them.

Accordingly, the present invention allows syringes used in a hospitals, etc. to be broken up so that they are not reusable, by a simple apparatus, and therefore, it is possible to eliminate the risks of reusing of syringes in narcotic crimes and of apreading virus, such as, for example, AIDS germs.

Accordingly, the present invention provides a syringe destruction apparatus to attain the above-mentioned objects, comprising a cam plate rotated by a motor disposed in a casing and rotating at a low speed, and a syringe needle shearing section and a barrel breaking section which are driven by the above-mentioned cam plate, wherein the above-mentioned shearing section includes a movable blade having a shaft part in sliding contact with one side of the above-mentioned cams and a stationary blade paired with the movable blade, the above-mentioned stationary blade is formed therein with a guide part for guiding the needle, and the above-mentioned barrel breaking section includes a movable blade having a shaft section in sliding contact with the other side of the above-mentioned cam plate and a stationary blade paired with the movable blade, thereby the movable blade of the above-mentioned syringe needle shearing section and the movable blade of the above-mentioned barrel breaking section carry out reciprocating rotation alternately.

It is noted that although ceramic materials are preferably used for the stationary blades and the movable blade in both syringe needle shearing section and barrel breaking section in order to prevent the blades from being rusted by liquid leaking from a syringe which has been broken, the present invention is not always limited to the use of ceramic materials for the blades. Materials other than ceramic materials, such as, for example, stainless steels and other steels, can also be used.

In the syringe destruction apparatus according to the present invention, since the cam plate is rotated by the motor to drive the needle shearing section and the barrel breaking section, alternately, the shearing of a needle and the breaking of the barrel are not carried out simultaneously. Accordingly, no large load is required to be put load is required on the motor, and therefore, the entire apparatus can be driven with a less power.

DETAILED DESCRIPTION OF THE EMBODIMENT

Figure 1:
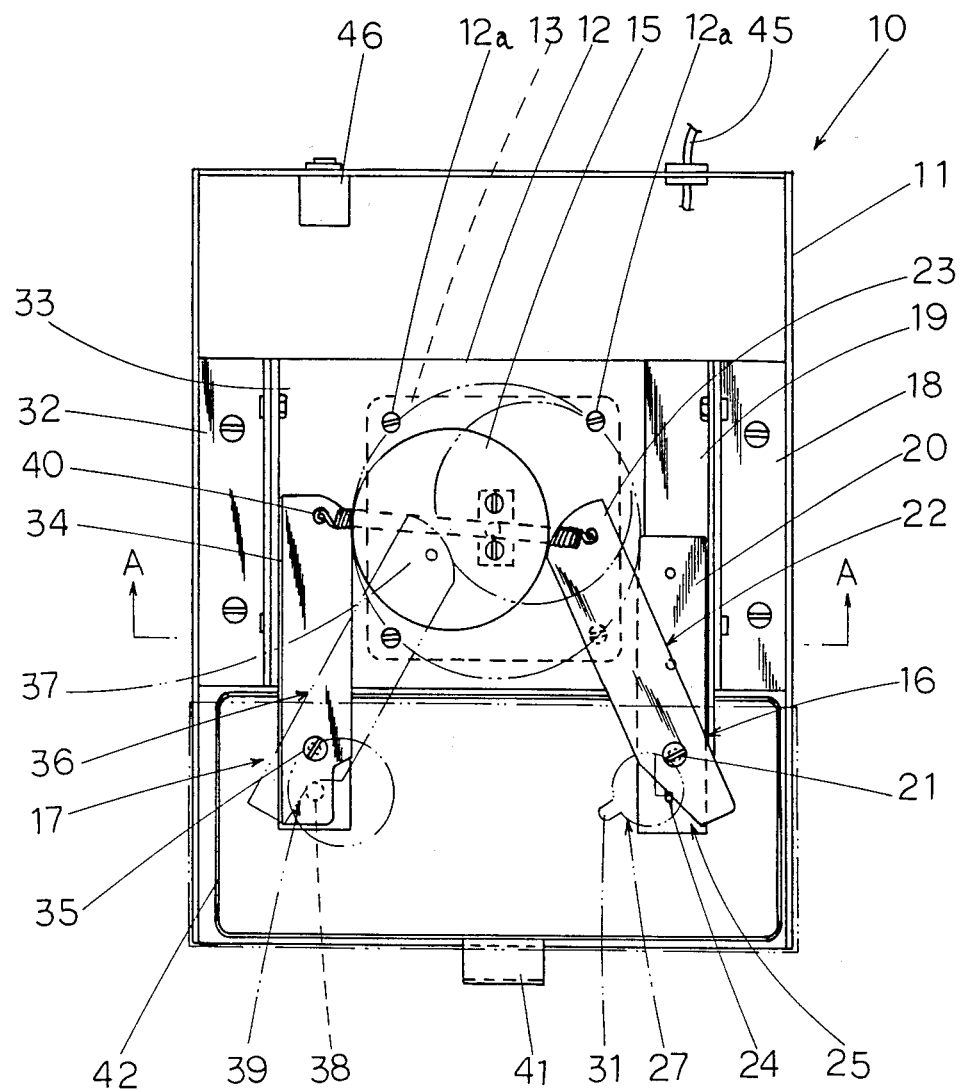
FIG. 1 is a plan view illustrating the interior structure of a syringe device in one embodiment form according to the present invention.
Figure 2:
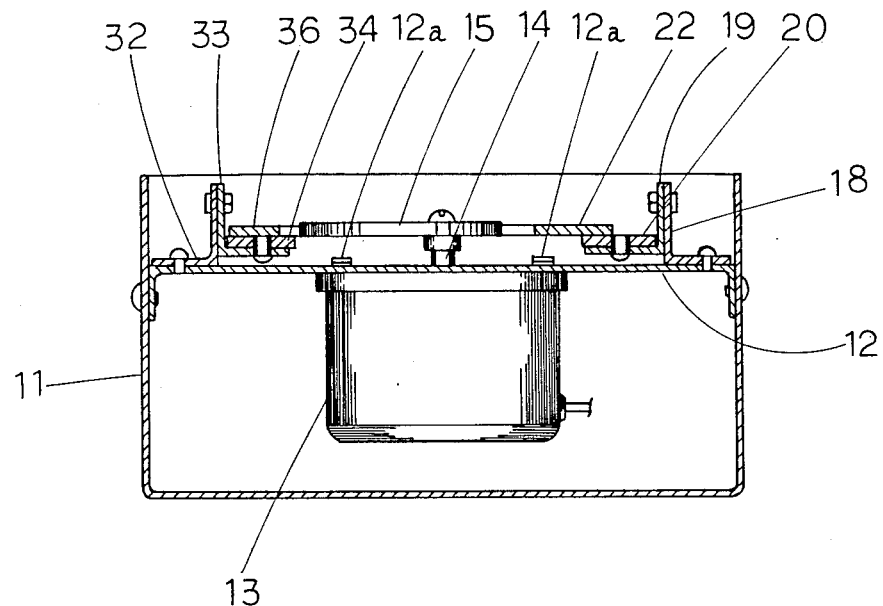
FIG. 2 is a cross-sectional view along the line A—A in FIG. 1.
Figure 3:
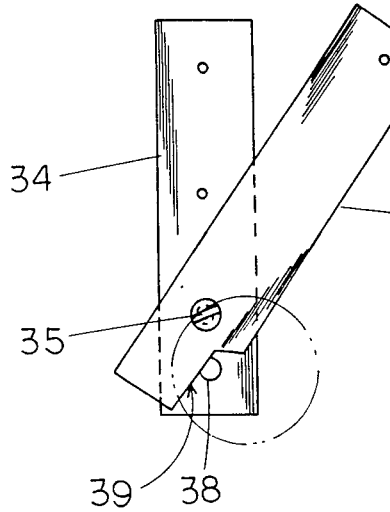
FIG. 3 is an enlarged plan view illustrating a barrel breaking section used in the above-mentioned embodiment.

Referring to FIGS. 1 and 2, a syringe destruction apparatus 10 in one embodiment form of the present invention is composed of a motor 13 attached to a section of a base plate 12 disposed in a casing 11, a cam plate 15 fitted onto the output shaft 14 of the motor 13, and a syringe needle shearing section 16 and a barrel breaking section 17 which are adapted to have sliding contact with the cam 18. The above-mentioned components are detailed hereinbelow.

The above-mentioned base plate 12 divides the casing 11 into two upper and low sections, and is attached thereon with the above-mentioned motor 13 at the lower section of the latter by screws 12 such that the output shaft 14 alone projects from the upper surface of the base plate 12. It is noted that the above-mentioned base plate 12 has in a wide channel-like shape as shown in FIG. 2, and is fixed at both ends thereof to the casing 11 by screws.

The output shaft 14 of the above-mentioned motor 13 which is fitted thereon with the disc-like cam plate 15, is set at a position which is eccentric from the center of the cam plate 15 by about one-half of the diameter thereof so that the cam plate can be turned eccentrically.

The syringe needle shearing section 16 and the barrel breaking section 17 are arranged on both sides of the above-mentioned cam 15, the syringe needle shearing section 16 including a stationary blade 20 attached to the base plate 12 through the intermediary of angle-like shape support members 18, 19 by screws, and a movable blade 22 paired with the stationary blade 20 and rotated about a pin 21 as a center fitted on the stationary blade 20.

The shaft part of the above-mentioned movable blade 22 is made to have sliding contact with the outer peripheral part of the above-mentioned cam plate 15, and is reciprocatingly rotated about the pin 21 in association with the rotation of the cam plate 15.

The above-mentioned stationary blade 20 is made of hard ceramic materials (for example, $ZrO_2$, $Al_2O_3$, Si$_3$N$_3$, SiC), and the cutting edge 24 thereof is composed of a circular hole having a diameter of about 2 to 3 mm. Further, the movable blade 22 attached to the stationary blade 20 by the pin 21 is also made of ceramic materials, and the cutting edge part 25 has an arcuated shape so that the movable blade 22 is reciprocatingly rotated to slide on the stationary blade 20 to cut a syringe needle fitted into the cutting edge part 24 of the stationary blade 20 by its shearing forth.

Figure 4:
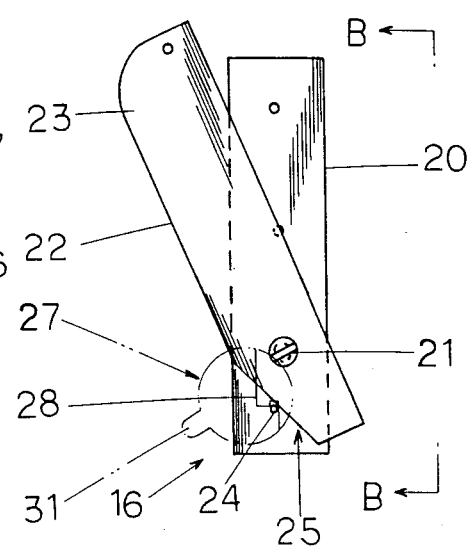
FIG. 4 is an enlarged plan view illustrating a syringe needle shearing section used in the above-mentioned embodiment.
Figure 5:
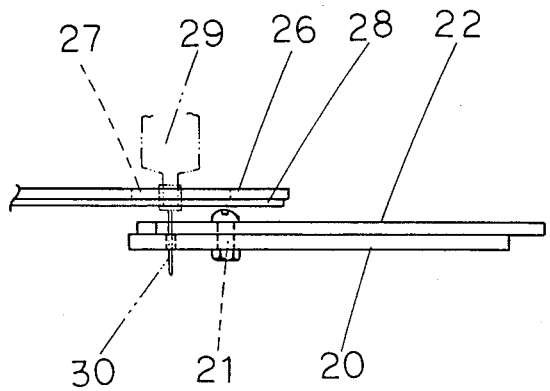
FIG. 5 is a lateral view along the line B—B in FIG. 4.
Figure 6:
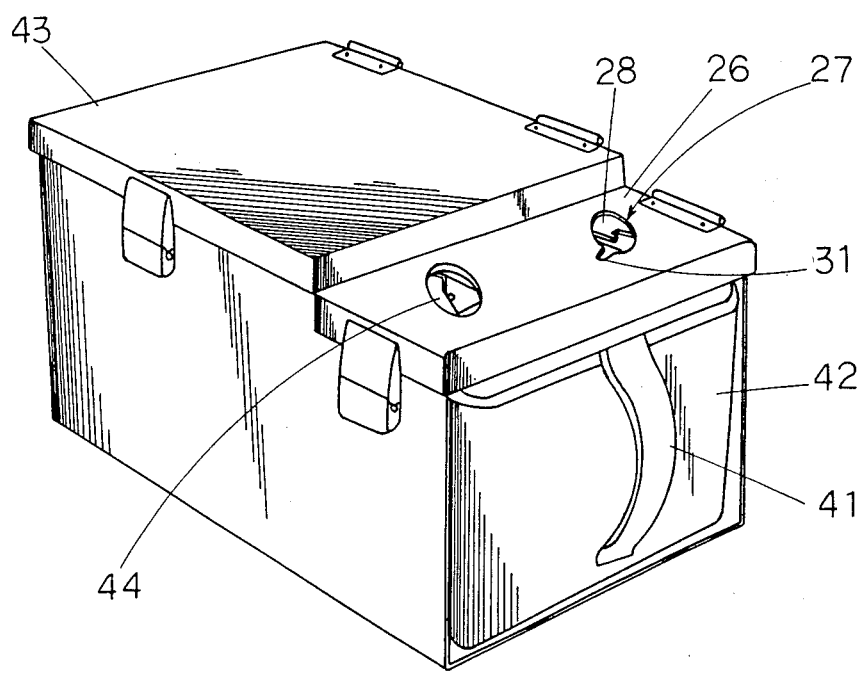
FIG. 6 is an external perspective view illustrating the syringe destruction apparatus relating to the above-mentioned embodiment.

Referring to FIG. 6, an opening cover 26 is attached to the upper part of the syringe needle shearing section 16, a syringe needle insertion hole 27 is formed in the cover 26. As shown in FIGS. 4, 5 and 6, a guide plate 28 is applied to the syringe needle insertion hole 27, and therefore, the syringe needle 30 attached to the syringe barrel is introduced along the guide plate 28 so that it is fitted into the cutting edge section 24 in the shape of the circular hole.

The above-mentioned syringe needle insertion hole 27 is formed therein with a transverse hole 31 for removing the syringe needle 30 having been sheared, as shown in FIGS. 4 and 6.

The above-mentioned barrel breaking section 17 is composed of a stationary blade 34 attached to the base plate through the intermediary of support members 32, 33 by screws, and a movable plate 36 is rotatably attached to the stationary blade 34 by a pin 35, the shaft section 37 of the movable plate 36 in sliding contact with the outer peripheral part of the cam plate 15 and reciprocatingly rotated about the pin 21 as a center in association with the rotation of the cam plate 15.

The cutting edge part 38 of the stationary blade 34 is formed with a circular hole having a diameter of about 5 to 6 mm while the cutting edge part 36 of the above-mentioned movable blade 39 is formed of a straight edge (although it is possible to use a slightly curved edge). With this arrangement, the tip of a syringe needle which is not shown is fitted into the cutting edge 38 and is then cut by the cutting edge 39 of the movable blade 36 which slides in a reciprocating fashion.

Further, as shown in FIG. 1, the shaft parts 23, 37 of the movable blades 22, 36 are coupled with each other by a tension spring 40, and therefore, are made to abut against the cam plate 15 with sufficient pushing force. Accordingly, the shaft parts 23, 37 of the movable blades 22, 36 are reciprocated in sliding contact with the cam plate 15 to alternately perform cutting operations so that both their loads are prevented from being exerted simultaneously to the motor 13.

As shown in FIGS. 1 and 6, below the above-mentioned syringe needle shearing section 16 and barrel breaking section 7, there is disposed a paper receiving container 42 with a handle 41 for storing sheared syringe needles and barrels whose front ends are cut and broken.

A cover 43 and the above-mentioned cover 26 are arranged on the upper section of the above-mentioned casing 11 as shown in FIG. 6, to protect the devices therein, and further, a barrel insertion hole 44 for receiving therein the front end part of the barrel 29 is formed in the cover 26 in addition to the syringe needle insertion hole 27.

Further, as shown in FIG. 1, there are arranged a cord 45 for supplying power to the motor 13 and a switch 46 connected to the cord 45 for energizing and deenergizing the motor 13 in the rear section of the casing 11.

When the above-mentioned syringe destruction apparatus is used, the switch 46 is first turned on to rotate the motor 13 at a low speed (60 rpm), and thereby the cam plate 15 is rotated. Accordingly, the movable blade 22 of the syringe needle shearing section 15 and the movable blade 36 of the barrel breaking section 17 are reciprocated, thereby preparations for the operation of the apparatus have been completed.

Then a used syringe is disposed of in the apparatus. The syringe needle 30 is first inserted into the syringe needle insertion hole 27 with the barrel 29 being left to be fitted in the needle 30 as shown in FIG. 5, and is moved along the guide plate 28. When the needle 30 is fitted into the cutting edge section 24 formed with a circular hole, the needle 30 is cut at its middle section by a shearing force in association with the reciprocating motion of the movable plate 22.

The barrel 29 with the needle 30 is transversely moved directly in this condition into the above-mentioned transverse hole 31, and when the barrel 29 is pulled after the root section of the needle 30 engaged in the transverse hole 31, the cut needle 30 is removed from the barrel 29, and then drops below into the receiving container 42.

Thereafter, the front end of the barrel 29 is inserted into the above-mentioned barrel insertion hole 44 and then fitted into the cutting edge section 38 formed with a circular hole, and then is cut in association with the reciprocating motion of the movable blade 36, thereby it is possible also to prevent the barrel 29 from being reused.

Further, the cut syringe needle 30 and barrel 29 drop into the receiving container 42 therebelow, and therefore, they can be discarded at a suitable time.

As explained in the above-mentioned embodiment, hard ceramic blades are used for the stationary blades 20, 34 and the movable blades 22, 36, and therefore, they are durable for a long life without rusting. However, stainless steel blades which do not rust easily can also be used with similar technical effects.

Further, it has been explained in the above-mentioned embodiment that the cutting edges 24, 38 of the stationary blades in both syringe needle shearing section and barrel breaking section are formed as circular holes. However, the present invention is not limited to such circular shape cutting edges, and it is possible to use straight cutting as are used in scissors.

What is claimed is:

1. A syringe destruction apparatus including a cam plate disposed in a casing and rotated by a motor rotating at a low speed, and a syringe needle shearing section and a barrel breaking section which are driven by the said cam plate, characterized in that the said syringe needle shearing section comprises a movable blade having a shaft part in sliding contact with one side of the said cam plates, a stationary blade paired with the movable blade and a guide part formed in the stationary blade, for guiding a syringe needle, and the said barrel breaking section comprises a movable blade having a shaft part in sliding contact with the other side of the said cam plate and a stationary blade paired with the said movable blade, thereby the movable blades in the said syringe needle shearing section and said barrel breaking section alternately carry out reciprocating rotation in association with the rotation of the said cam plate.

2. A syringe destruction apparatus as set forth in claim 1, wherein the said stationary blades in the said syringe needle shearing section and the said barrel breaking section have cutting edges which are formed of circular holes.

3. A syringe destruction apparatus as set forth in claim 1 or 2, wherein the said stationary and movable blades in the said syringe needle shearing section and the said barrel breaking section are made of ceramic materials.

* * * * *